(12) United States Patent
Smith

(10) Patent No.: US 8,997,736 B2
(45) Date of Patent: Apr. 7, 2015

(54) INTERFACE APPARATUS IDENTIFICATION SYSTEM AND METHOD AND DIFFERENTIATING FEATURE THEREFOR

(75) Inventor: David W. Smith, Oakmont, PA (US)

(73) Assignee: Koninklijke Philips N.V., Eindhoven (NL)

( * ) Notice: Subject to any disclaimer, the term of this patent is extended or adjusted under 35 U.S.C. 154(b) by 965 days.

(21) Appl. No.: 13/131,630

(22) PCT Filed: Nov. 21, 2009

(86) PCT No.: PCT/IB2009/055253
§ 371 (c)(1),
(2), (4) Date: May 27, 2011

(87) PCT Pub. No.: WO2010/070494
PCT Pub. Date: Jun. 24, 2010

(65) Prior Publication Data
US 2011/0232645 A1    Sep. 29, 2011

Related U.S. Application Data

(60) Provisional application No. 61/122,765, filed on Dec. 16, 2008.

(51) Int. Cl.
| | | |
|---|---|---|
| A61M 16/00 | (2006.01) | |
| A62B 9/00 | (2006.01) | |
| A62B 27/00 | (2006.01) | |
| G08B 3/00 | (2006.01) | |
| G08B 5/00 | (2006.01) | |
| A61M 16/06 | (2006.01) | |
| A61M 16/08 | (2006.01) | |

(52) U.S. Cl.
CPC .......... *A61M 16/06* (2013.01); *A61M 16/0816* (2013.01); *A61M 16/0875* (2013.01); *A61M 2205/6018* (2013.01); *A61M 2205/6081* (2013.01)

(58) Field of Classification Search
USPC ........................ 128/202.22, 205.25
See application file for complete search history.

(56) References Cited

U.S. PATENT DOCUMENTS

| | | | | |
|---|---|---|---|---|
| 5,714,121 A | * | 2/1998 | Alderete et al. | ........... 422/82.07 |
| 6,126,610 A | | 10/2000 | Rich | |
| 6,360,741 B2 | | 3/2002 | Truschel | |

(Continued)

FOREIGN PATENT DOCUMENTS

| | | |
|---|---|---|
| EP | 1731188 A2 | 12/2006 |
| WO | WO03102111 A1 | 12/2003 |
| WO | WO2006092001 A1 | 9/2006 |

*Primary Examiner* — Justine Yu
*Assistant Examiner* — Kathrynn Reilly
(74) *Attorney, Agent, or Firm* — Michael W. Haas

(57) ABSTRACT

An interface apparatus identification system for a respiration machine such as, for example, a medical ventilator, includes a detection element which is adapted to communicate with the ventilator, a patient interface assembly including a patient interface apparatus for delivering a flow of gas from the ventilator to an airway of a patient, and a differentiating feature which is incorporated into the patient interface assembly. The patient interface apparatus is selected from a predetermined category such as, for example, a specific make or brand. The differentiating feature is detectable by the detection element to distinguish patient interface apparatus that fall within the predetermined category from those that do not. Operation of the respiration machine in conjunction with the patient interface apparatus is dependent upon detection of the differentiating feature by the detection element. An associated identification method is also disclosed.

6 Claims, 5 Drawing Sheets

(56) References Cited

U.S. PATENT DOCUMENTS

| | | |
|---|---|---|
| 6,716,368 B1 | 4/2004 | Schottland |
| 7,043,979 B2 * | 5/2006 | Smith et al. ............... 73/204.14 |
| 2007/0175471 A1 | 8/2007 | Schermeier |
| 2007/0272240 A1 * | 11/2007 | Aylsworth et al. ....... 128/204.18 |
| 2007/0277824 A1 | 12/2007 | Aylsworth |
| 2008/0053446 A1 * | 3/2008 | Sleeper et al. ........... 128/205.25 |
| 2010/0147301 A1 * | 6/2010 | Kwok ...................... 128/204.21 |

* cited by examiner

INTERFACE APPARATUS IDENTIFICATION SYSTEM AND METHOD AND DIFFERENTIATING FEATURE THEREFOR

CROSS-REFERENCE TO RELATED APPLICATIONS

This patent application claims the priority benefit under 35 U.S.C. §119(e) of U.S. Provisional Application No. 61/122,765 filed on Dec. 16, 2008, the contents of which are herein incorporated by reference.

CROSS-REFERENCE TO RELATED APPLICATIONS

1. Field of the Invention

The disclosed concept relates generally to interface apparatus and, more particularly, to an identification system and method for identifying specific patient interface apparatus for use with a respiration machine to deliver a breathable gas to a patient. The disclosed concept also relates to differentiating features for interface apparatus identification systems.

BACKGROUND INFORMATION

As shown in FIG. 1, systems for delivering breathable gas to an airway 2 of a patient 4 to treat a medical disorder typically include a respiration machine 10 (e.g., without limitation, a medical ventilator; a non-invasive ventilator (NIV) such as, for example and without limitation, a CPAP machine), a patient interface apparatus 12 and an air delivery conduit extending therebetween.

In the example of FIG. 1, the patient interface apparatus is a respiratory mask 12 and the opposing ends 16,18 of the conduit 14 include connectors 20,22. The first connector 20 is structured to connect the first end 16 of the conduit 14 to a receptacle 24 of the respiration machine 10, and the second connector 22 is structured to connect the second end 18 of the conduit 14 to a separate swivel 26, which is in turn connected to an elbow 28 of the mask 12.

A wide array of mask types, shapes and sizes are available from a variety of different manufacturers and, in general, the aforementioned components (e.g., conduit 14; swivel 26) are readily interchangeable such that any of a wide variety of different masks (e.g., 12) can be coupled to the respiration machine 10 for use therewith. For example, the conduit connectors 20,22, machine receptacle 24, swivel 26 and mask elbow 28 typically have standard dimensions (e.g., without limitation, the receptacle 24 and swivel 26 typically have an outer diameter (OD) of about 22 mm). However, it is necessary to ensure that the mask 12 or other suitable patient interface apparatus (not shown) is compatible with the respiration machine 10. That is, to function properly, the mask 12 must be properly identified and characterized by (e.g., synchronized with) the respiration machine 10, for example, to provide the necessary flow compensation in order for the patient 4 to receive the appropriate therapy. There is a desire to control this identification and characterization process, for example, so that only a specific make or brand of patient interface apparatus (e.g., without limitation, mask) will be identified and accepted for use with the respiration machine and in differentiating features therefor.

SUMMARY OF THE INVENTION

These needs and others are met by embodiments of the disclosed concept, which are directed to a patient interface apparatus identification system and method, including a differentiating feature that is incorporated into at least one component of a patient interface assembly and is detectable to identify and distinguish patient interface apparatus that fall within a predetermined category for use with the respiration machine.

As one aspect of the disclosed concept, an interface apparatus identification system is provided for a respiration machine. The respiration machine is adapted to generate a flow of gas. The interface apparatus identification system comprises: a detection element adapted to communicate with the respiration machine; a patient interface assembly comprising a patient interface apparatus for delivering the flow of gas to an airway of a patient, the patient interface apparatus being selected from a predetermined category; and a differentiating feature incorporated into the patient interface assembly to distinguish patient interface apparatus that fall within the predetermined category from patient interface apparatus that do not fall within the predetermined category. Operation of the respiration machine in conjunction with the patient interface apparatus is dependent upon detection of the differentiating feature by the detection element.

As another aspect of the disclosed concept, a differentiating feature is provided for an interface apparatus identification system. The interface apparatus identification system includes a detection element adapted to communicate with a respiration machine, and a patient interface assembly comprising a patient interface apparatus for delivering a flow of gas from the respiration machine to an airway of a patient. The patient interface apparatus is selected from a predetermined category. The differentiating feature comprises: a predetermined material property incorporated into at least one component of the patient interface assembly, the material property being exhibited when the at least one component is exposed to a predetermined condition. The predetermined material property is detectable by the detection element of the respiration machine to distinguish patient interface apparatus that fall within the predetermined category from patient interface apparatus that do not fall within the predetermined category, and operation of the respiration machine in conjunction with the patient interface apparatus is dependent upon detection of the predetermined material property.

As another aspect of the disclosed concept, an interface apparatus identification method comprises: (a) providing a patient interface assembly, the patient interface assembly comprising: (1) a patient interface apparatus adapted to deliver a flow of gas to an airway of a patient, the patient interface apparatus being selected from a predetermined category, (2) a detection element adapted to communicate with a respiration machine, and (3) a differentiating feature incorporated into the patient interface assembly; (b) coupling the patient interface assembly to the respiration machine; and (c) detecting with the detection element if the differentiating feature of the patient interface assembly is present, thereby falling within the predetermined category, (1) if yes, approving the patient interface apparatus for operation with the respiration machine, (2) if no, prohibiting operation of the respiration machine absent a predetermined user input.

BRIEF DESCRIPTION OF THE DRAWINGS

A full understanding of the disclosed concept can be gained from the following description of the preferred embodiments when read in conjunction with the accompanying drawings in which.

DESCRIPTION OF THE PREFERRED EMBODIMENTS

For purposes of illustration, embodiments of the disclosed concept will be described as applied to a respiratory mask, although it will become apparent that they could also be applied to identify and differentiate any known or suitable patient interface apparatus adapted for use with a respiration machine.

As employed herein, the term "patient interface apparatus" refers to any known or suitable mechanism for establishing fluid communication between the respiration machine (e.g., without limitation, a medical ventilator; a non-invasive ventilator (NIV) such as, for example and without limitation, a CPAP machine) and an airway of a patient, and expressly includes, but is not limited to, non-invasive patient interfaces such as masks, nasal canulas, combination nasal/oral masks, and removable mouth pieces, and invasive patient interfaces such as tracheal tubes and endotracheal tubes, as well as humidifiers, nebulizers and meter dose inhalers, which can be invasive or non-invasive.

As employed herein, the term "detection element" refers to any known or suitable mechanism or sensing element (e.g., without limitation, sensor; photo-eye) for detecting a differentiating feature (e.g., identifying characteristic such as, for example and without limitation, color; florescence; electrical resistance) associated with a predetermined category (e.g., without limitation, make or brand; any known or suitable patient interface assembly or patient interface apparatus operation parameter such as, for example and without limitation, resistance to airflow, exhalation leak rate or any other known or suitable parameter) of patient interface apparatus.

As employed herein, the terms "fluoresce", "fluorescent" and "fluorescence" refer to the optical characteristic(s) of a particular material or component when it is exposed to a predetermined condition. For example and without limitation, certain polycarbonate materials are designed to fluoresce a specific color when they are exposed to light having a specific wavelength.

As employed herein, the statement that two or more parts are "coupled" together shall mean that the parts are joined together either directly or joined through one or more intermediate parts.

As employed herein, the term "number" shall mean one or more than one (i.e., a plurality).

Figure 2:
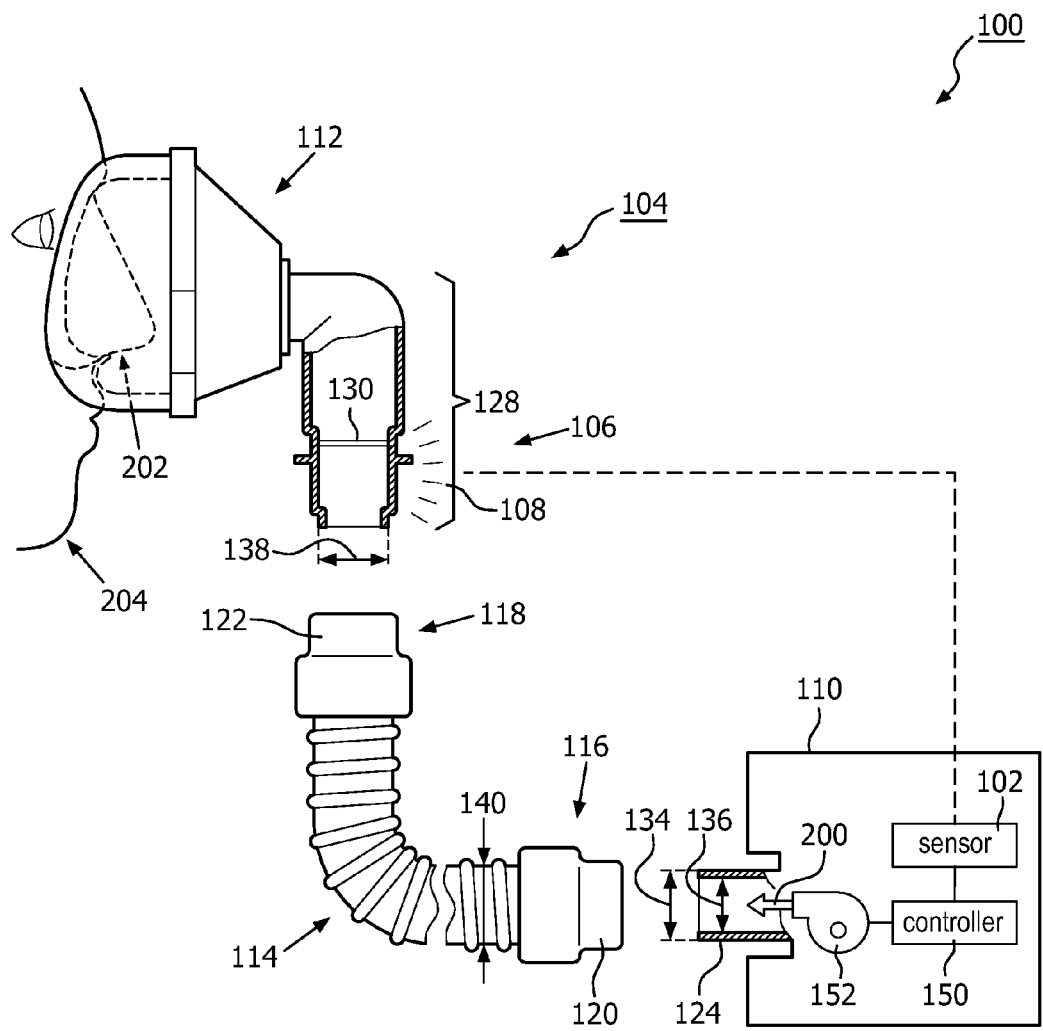
FIG. 2 is an exploded, partially in section side elevation view of an interface apparatus identification system and differentiating feature therefor, in accordance with an embodiment of the disclosed concept.

FIG. 2 shows an interface apparatus identification system 100 for a respiration machine such as, for example and without limitation, a medical ventilator 110 (shown in simplified form). Operation of medical ventilators (e.g., 110) to generate a flow of gas (indicated generally by arrow 200 in FIG. 2) for delivery to an airway 202 (shown in hidden line drawing in FIG. 2) of a patient 204, is generally well known. Among other components, the ventilator 110 includes a controller 150, which communicates with a flow generator 152 to generate the aforementioned flow of gas 200. For ease of illustration and economy of disclosure, the ventilator 110 and components (e.g., sensor 102; controller 150; flow generator 152) are shown in simplified form.

The interface apparatus identification system 100 includes a detection element 102 (e.g., without limitation, sensor), which is adapted to communicate with the controller 150 of the ventilator 110, and a patient interface assembly 104, which includes a patient interface apparatus 112 for delivering the flow of gas 200 from the ventilator 110 to the airway 202 of the patient 204. As will be described in greater detail hereinbelow, the patient interface apparatus 112 is selected from a predetermined category. A differentiating feature 106 is incorporated into at least one component of the patient interface assembly 104 to distinguish patient interface apparatus 112 that fall within such predetermined category from those that do not. As will also be described, operation of the ventilator 110 in conjunction with the patient interface apparatus 112, is dependent upon detection of the differentiating feature 106 by the detection element 102.

Accordingly, it will be appreciated that the disclosed concept provides a system 100 and method 160 (described hereinbelow with respect to FIG. 5) for relatively quickly and easily controlling which patient interface apparatus are suitably operable with a given respiration machine (e.g., medical ventilator 110). That is, for example and without limitation, the aforementioned predetermined category of patient interface apparatus may be a specific make or brand of patient interface apparatus (e.g., patient interface apparatus that are manufactured and/or sold by a particular company), wherein the ventilator 110 will only operate in the desired manner with the specific brand of patient interface apparatus (e.g., 112). It will be appreciated, however, that a "predetermined category" in accordance with the disclosed concept may alternatively, or additionally, be any known or suitable patient interface assembly or patient interface apparatus operation parameter such as, for example and without limitation, resistance to airflow, exhalation leak rate or any other known or suitable parameter. Thus, it will be appreciated that the differentiating feature (e.g., 106) in accordance with the disclosed concept facilitates the identification and distinction of one or more attributes of the patient interface assembly (e.g., 104).

Figure 1:
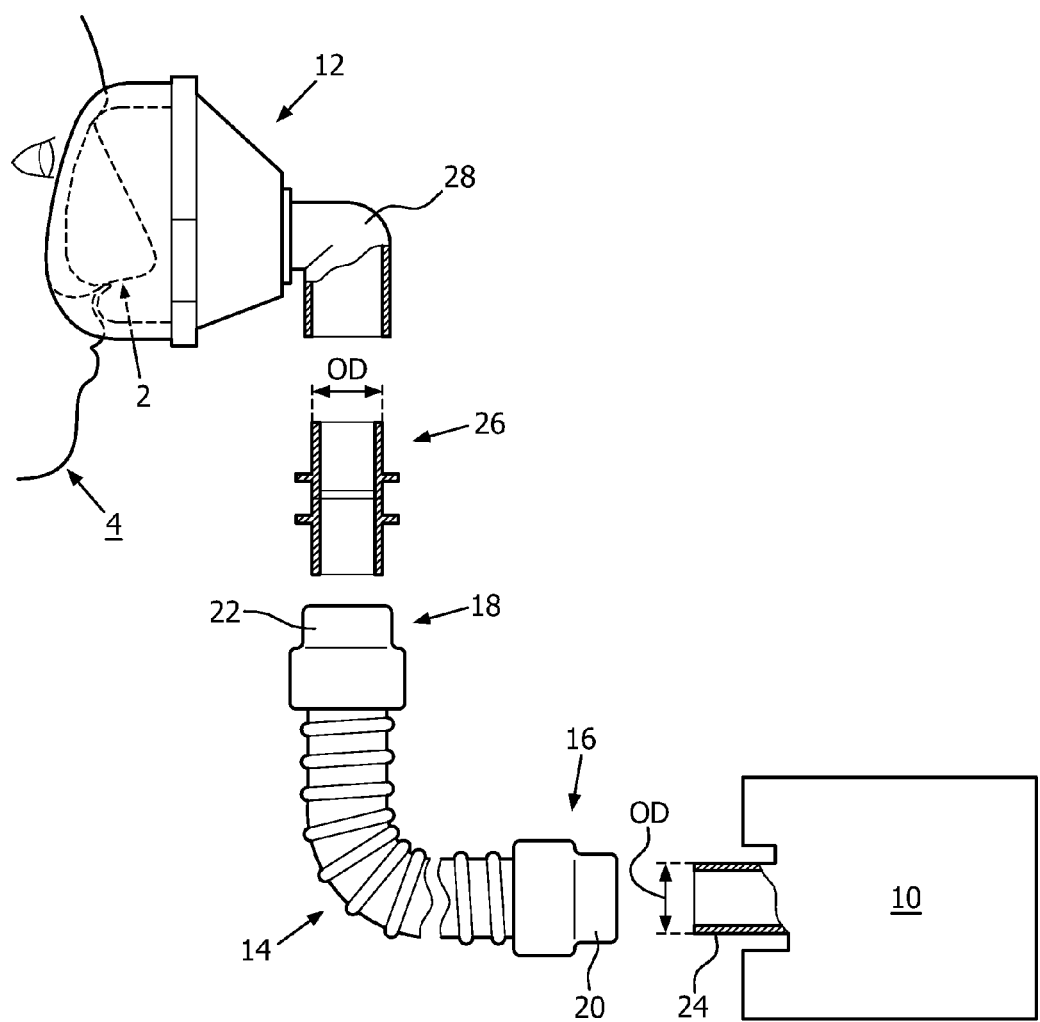
FIG. 1 is a partially exploded, partially in section side elevation view of an interface apparatus system.

In the example of FIG. 2, the patient interface assembly 104 further includes a conduit 114 having first and second opposing ends 116,118. A first connector 120 is structured to connect the first end 116 of the conduit 114 to a corresponding receptacle 124 of ventilator 110. A second connector 122 connects the second end 118 of conduit 114 to the respiratory mask 112. The example respiratory mask 112 includes an elbow 128 having an integral swivel 130. That is, the elbow 128 and integral swivel 130 thereof collectively form a molded extension of the respiratory mask 112, as shown. Accordingly, it will be appreciated that the molded extension 128,130 is connectable directly to the corresponding connector 122 of the conduit 114, without requiring a separate adapter or swivel element therebetween (see, for example, separate swivel 26 disposed between the conduit 14 and elbow 28 in FIG. 1). Thus, the swivel 130 is "integral" with the elbow 128 in the respect that the elbow 128 contains the swivel 130, as opposed to there being two separate components that are subsequently joined together.

The swivel 130 enables pivotal movement of the respiratory mask 112, for example, with respect to the corresponding conduit connector 122 and conduit 114, without requiring a separate swivel (see, for example, separate swivel 26 of FIG. 1) therebetween. Among other benefits, this elbow/swivel assembly 128,130 reduces the number of parts of the patient interface assembly 104, and reduces the number of connections (e.g., joints) between the ventilator 110 and mask 112. This, in turn, advantageously reduces the potential for leaks which can occur at such connections. It will, however, be appreciated that the disclosed interface apparatus identification system 100 and method 160 (FIG. 5) can be employed with any known or suitable alternative type and/or configuration of patient interface apparatus (not shown).

In one non-limiting embodiment of the disclosed concept, the differentiating feature 106 is a material property, which is exhibited when the component or components of the patient interface assembly 104 that possess such material property is/are exposed to a predetermined condition. In FIG. 2, for example, the differentiating feature 106 is incorporated into the mask 112 of the patient interface assembly 104, and the material property is that the mask fluoresces a predetermined color (see, for example, the fluorescence indicated generally by reference 108 in FIG. 2) when it is exposed to light having a preselected wavelength. More specifically, the mask 112 is made from a material (e.g., without limitation, plastic) that is adapted to change color (e.g., without limitation, fluoresce) when exposed to such light (e.g., without limitation, ultraviolet (UV) light). For example, in one non-limiting embodiment, the mask 112 changes from being clear, translucent or generally devoid of color to fluorescing a green color when activated by the specific light. However, it will be appreciated that the material could be formulated to have any known or suitable alternative color change or combination of color changes (e.g., without limitation, shades of color), without departing from the scope of the disclosed concept. It will also be appreciated that the material may be made to activate (e.g., without limitation, fluoresce) only at the a preselected wavelength, or to react differently when exposed to each of a number of different preselected wavelengths.

The detection element (e.g., sensor 102) of the ventilator 110 is adapted to detect the particular fluorescence and communicate with the controller 150 to evaluate whether or not it corresponds to the aforementioned predetermined category of patient interface apparatus 112. If so, the mask 112 is suitable for operation with the ventilator 110. This identification method is further described in greater detail hereinbelow with reference to FIG. 5.

Figure 3:
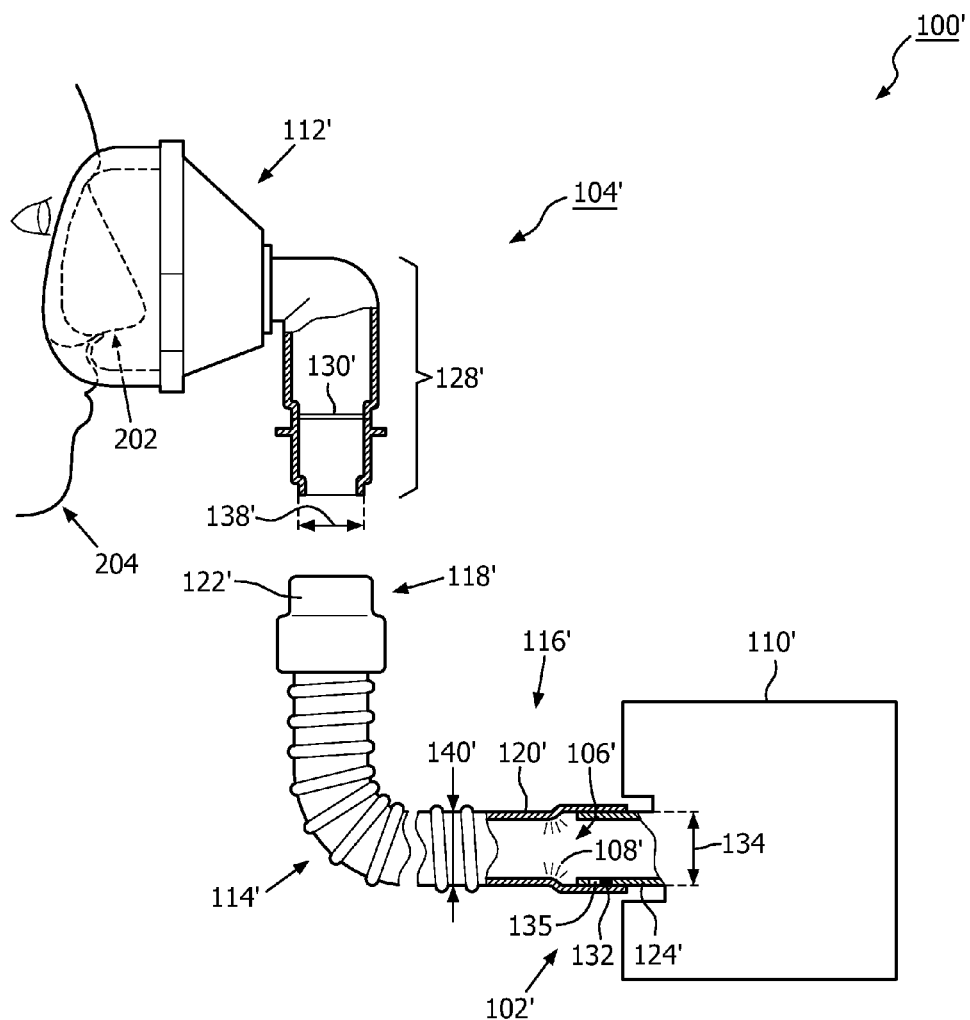
FIG. 3 is a partially exploded, partially in section side elevation view of an interface identification system and differentiating feature therefor, in accordance with another embodiment of the disclosed concept.

As shown in the non-limiting example embodiment of FIG. 3, the sensor 102' is disposed proximate to the receptacle 124' of the ventilator 110' and includes a photo eye 132 for detecting the aforementioned fluorescence 108' (see also fluorescence 108 of FIG. 2). In FIG. 3, the ventilator 110' also includes a light 135 (e.g., without limitation, UV light source; light emitting diode (LED); black light), which emits light having the preselected wavelength or other necessary attribute to trigger or activate such fluorescence 108' (see also fluorescence 108 of FIG. 2). It will, however, be appreciated that the light 135 or other known or suitable exposure apparatus (not shown) could alternatively be disposed elsewhere (e.g., without limitation, on another component of the interface apparatus identification system 100'; separate from the system 100').

Continuing to refer to FIG. 3, it will be appreciated that the differentiating feature 106' may alternatively or additionally be incorporated into another component of the patient interface assembly 104'. For example and without limitation, in FIG. 3, the differentiating feature 106' is incorporated in the first connector 120'. Specifically, when the first connector 120' is attached to the ventilator receptacle 124' and is exposed to the light 135, the first connector 120' fluoresces the aforementioned predetermined color (indicated generally by reference 108' in FIG. 3), which is detected by the photo-eye 132. In the example of FIG. 3, the first connector 120' is molded directly into the first end 116' of the conduit 114', as shown, although a separate connector (see, for example, connector 120" of FIG. 4) is also within the scope of the disclosed concept. Accordingly, unlike the embodiment of FIG. 2 wherein the differentiating feature 106 was employed in the respiratory mask 112, in the example of FIG. 3, the differentiating feature 106' is instead incorporated into a portion of the conduit 114' and, in particular, as a material property of the first connector 120' thereof. It will, however, be appreciated that the fluorescence 108' (see also fluorescence 108 of FIG. 2) and/or any other known or suitable differentiating feature 106" (e.g., for example and without limitation, electrically conductive coating 108" described hereinbelow with respect to FIG. 4) could be employed in one or more of the components (e.g., without limitation, mask 112'; conduit 114'; connector 120') of the patient interface assembly 104'.

Also in FIG. 3, as will be discussed in greater detail hereinbelow, it will be appreciated that the outer diameter (OD) 140' of the conduit 114' is smaller than the OD 140 of conduit 114 in the example of FIG. 2. For example and without limitation, the OD 140' is about 15 mm, whereas the OD 140 in the example of FIG. 2 is about 20 mm. As will be described, this unique size of the conduit 114' and/or the integral connector 120' therefor, can serve to further differentiate the patient interface assembly 104'.

The example fluorescent material property 108 (FIG. 2), 108' (FIG. 3) will now be described in greater detail. Specifically, certain materials such as, for example and without limitation, specialized polycarbonates change color (e.g., fluoresce) when exposed to a specific light (e.g., UV or black light of a predetermined wavelength). That is, under normal circumstances, in the absence of such exposure, the component has a normal appearance (e.g., transparent; translucent; generally devoid of fluorescence). However, upon exposure to the specific light condition, the component fluoresces a specific color. Suitable polycarbonate materials and color effects therefor are disclosed, for example, in U.S. Pat. No. 6,716,368 and WO 2003/102,111, which are hereby incorporated herein by reference.

Figure 4:
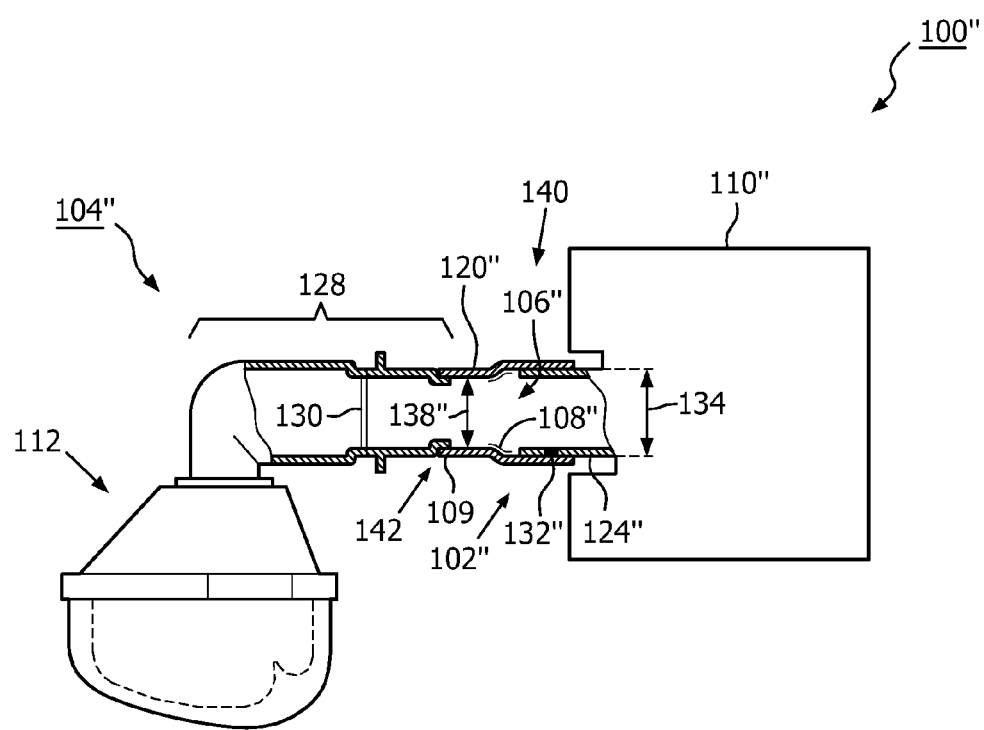
FIG. 4 is a partially in section side elevation view of an interface identification system and differentiating system therefor, in accordance with another embodiment of the disclosed concept.

In accordance with the disclosed concept, this fluorescence is detectable by the aforementioned detecting element (e.g., without limitation, sensor 102 of FIG. 2; see also photo-eye 132 of FIG. 3 and photo-eye 132" of FIG. 4) and, therefore, is associated with the predetermined category (e.g., without limitation, specific brand or make; or resistance to airflow, exhalation leak rate or any other known or suitable parameter) of patient interface apparatus 112 (FIGS. 2 and 4), 112' (FIG. 3) for the purpose of accepting or rejecting it for operation with the ventilator 110 (FIG. 2), 110' (FIG. 3), 110" (FIG. 4). It will, therefore, be appreciated that one or more of the components (e.g., without limitation, mask 112; conduit 114; connectors 120,122) could be made to exhibit a specific fluorescence 108 (FIG. 2), 108' (FIG. 3) or color change that is unique to these specific brand or make of mask 112 (FIGS. 2 and 4), 112' (FIG. 3) or other suitable patient interface apparatus (not shown), as defined herein. Thus, the ventilator 110 (FIG. 2), 110' (FIG. 3), 110" (FIG. 4) can be rendered inoperable with any other brand or make of patient interface apparatus (not shown), or with a patient interface apparatus having or not having any other known or suitable parameter falling within a predetermined category, as desired.

FIG. 4 shows another non-limiting alternative embodiment in accordance with the disclosed concept, wherein the mask 112 is connectable directly to a connector 120", which in turn is connectable directly to the receptacle 124" of the ventilator 110". The identification system 100" of FIG. 4 also illustrates an alternative differentiating feature 106", which can be employed instead of or in addition to the aforementioned fluorescence 108 (FIG. 2), 108' (FIG. 3). Specifically, the single connector 120" preferably includes an electrically conductive coating (indicated generally by reference 108" in FIG. 4), which has a predetermined electrical resistance that is detectable by the detection element 102" (e.g., without limitation, electrical conductor 132"). Other components of the patient interface assembly 104" may also include an electrically conductive coating for suitable detection by the detection element 102" and electrical communication with the conductor 132", as desired. In the example of FIG. 4, the elbow/swivel assembly 128,130 includes an electrically conductive coating (indicated generally by reference 109 in FIG. 4), which has substantially the same electrical resistance as coating 108" and, therefore, is electrically connectable therewith. Alternatively, the elbow/swivel assembly 128,130 and, in particular, the electrically conductive coating 109 thereof, could be directly connected to the ventilator receptacle 124" (such direct connection is not shown) for detection by the electrical conductor 132" of the connected detection element 102".

It will be appreciated that the fluorescence 108 differentiating feature 106 described with respect to the mask 112 with reference to FIG. 2 could be used in the embodiment of FIG. 4, without the aforementioned electrically conductive coating 108". That is, the mask 112 could be structured to fluoresce through the connector 120" of FIG. 4 to be detected by a photo-eye 132".

In addition to the foregoing, it will be appreciated that the various components of the patient interface assembly 104 (FIG. 2), 104' (FIG. 3), 104" (FIG. 4) may have a variety of specific sizes and structures to further distinguish and differentiate the predetermined category (e.g., without limitation, specific make or brand; any known or suitable patient interface assembly or patient interface apparatus operation parameter such as, for example and without limitation, resistance to airflow, exhalation leak rate or any other known or suitable parameter) of patient interface apparatus 112 (FIGS. 2 and 4), 112' (FIG. 3) from others. For example, in FIG. 2 the ventilator receptacle 124 has an outer diameter (OD) 134 and an inner diameter (ID) 136, which in accordance with one non-limiting embodiment are about 22 mm and about 19 mm, respectively, and the end of the mask elbow; 128 tapers to an outer diameter (OD) 138, which is also about 19 mm. Thus, it will be appreciated that the mask 112 can be employed with a conduit 114 having an outer diameter (OD) 140 of about 22 mm, which is a generally standard conduit dimension in the art. More specifically, the OD 138 of the unique mask elbow 128 permits it to be inserted into the second connector 122 of the conduit 114, for a direct connection thereto, or alternatively to be inserted directly into the ID 136 of the ventilator receptacle 124. Similarly, the OD 134 of the ventilator receptacle 124 is sized and configured to be inserted into the first connector 120 of the conduit 114 for direct connection thereto. It will, however, be appreciated that one or more of the components of the patient interface assembly 104 could be made to have a suitable alternative dimension and/or configuration, without departing from the scope of the disclosed concept.

For example and without limitation, in the non-limiting example embodiment of FIG. 3, the ventilator receptacle 124' has the same OD 134 as in the example embodiment of FIG. 2, previously discussed, and the end of the mask elbow 128' has the same OD 138', but the conduit 114' is configured differently. Specifically, the OD 140' of the conduit 114' is smaller than the OD 140 of conduit 114 of FIG. 2. For example and without limitation, in one non-limiting embodiment, the OD 140' is about 15 mm. This unique conduit dimension (e.g., without limitation, OD 140') necessitates a unique connector 120' to facilitate connection of the first end 116' of the conduit 114' to the ventilator receptacle 124'. A portion of the ventilator receptacle 124' and the connector 120' are shown in section view in FIG. 3 to illustrate this structural relationship. In the example of FIG. 3, the connector 120' is a molded extension of the conduit 114', although it will be appreciated that it could alternatively be a separate connector (see, for example, separate connector 120" of FIG. 4). The second connector 122', which is attached to the second end 118' of the conduit 114' is substantially similar in size to second connector 122 in the example of FIG. 2. Accordingly, it will be appreciated that the conduit 114', connector 120' therefor, and the reduced OD 138' of the mask elbow 128' are unique in size and configuration and, therefore, are only suitable for use with the predetermined category (e.g., without limitation, specific brand or make) of mask 112'.

Figure 5:
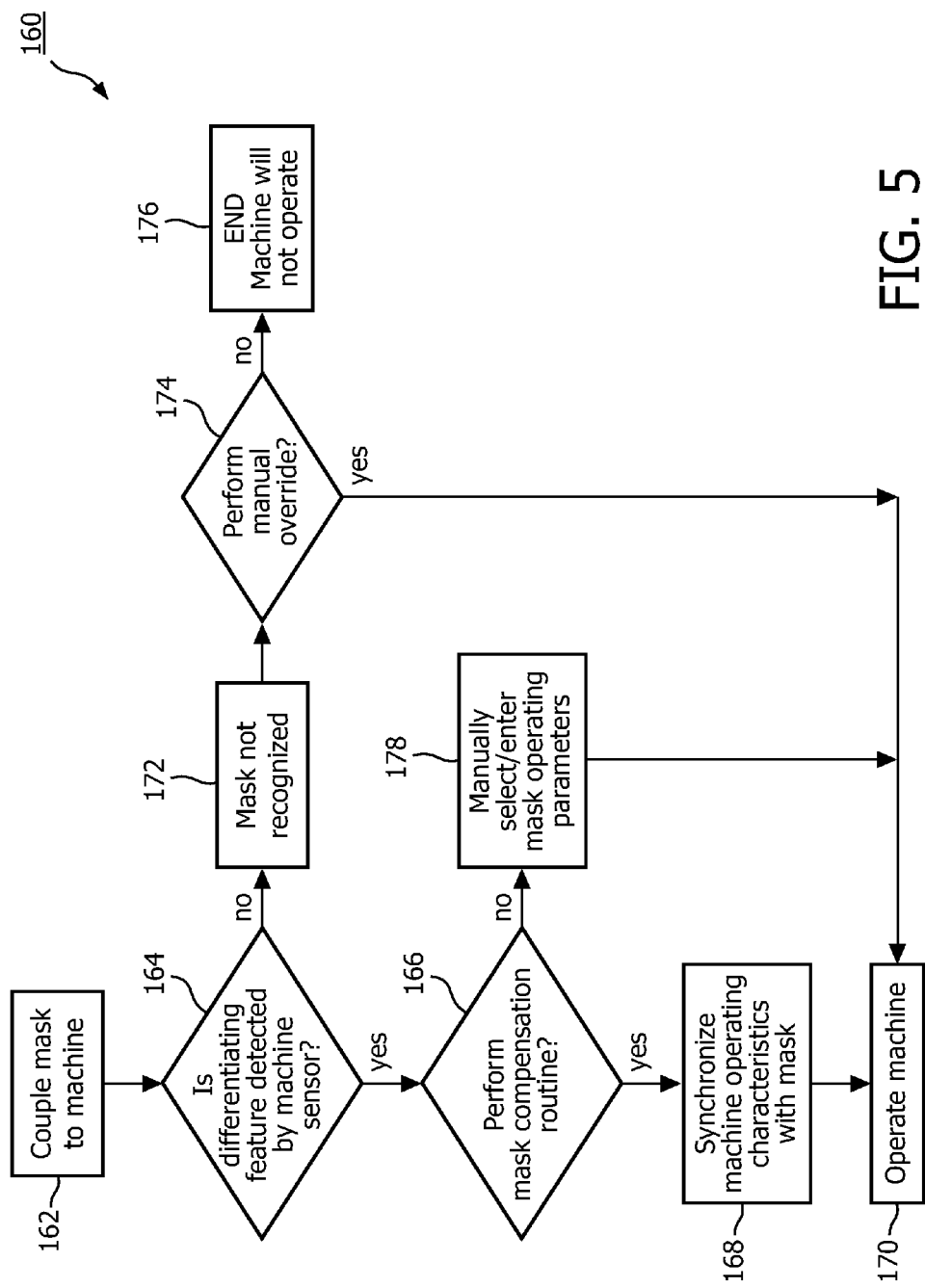
FIG. 5 is a flow diagram for an interface apparatus identification method, in accordance with an embodiment of the disclosed concept.

FIG. 5 shows a method 160 of identifying patient interface apparatus 112 (FIGS. 2 and 4), 112' (FIG. 3) for use with a particular respiration machine 110 (FIG. 2), 110' (FIG. 3), 110" (FIG. 4) in accordance with an embodiment of the disclosed concept. For economy of disclosure, the method 160 will be described with reference to the non-limiting embodiment of FIG. 2, although it will be appreciated that the following steps would be substantially similar for other embodiments in accordance with the disclosed concept. Specifically, at a first step 162, the patient interface apparatus 112 is coupled to the respiration machine 110. At step 164, the detection element (e.g., without limitation, sensor 102 of FIG. 2) of the respiration machine 110 detects if the differentiating feature 106 of patient interface assembly 104 is present, in which case the interface apparatus 112 falls within the predetermined category (e.g., specific brand or make of patient interface apparatus 112). Specifically, if the differentiating feature 106 is detected, then at step 166 the patient interface apparatus 112 is approved for operation with the respiration machine 110 and a determination of whether or not to perform an interface apparatus compensation routine is made. Such a compensation routine is disclosed, for example, and commonly assigned U.S. Pat. No. 6,360,741, which is hereby incorporated herein by reference. If so, at step 168 the respiration machine operating characteristics are synchronized with the patient interface apparatus 112. Finally, at step 170, the respiration machine 110 is operated to deliver the desired therapy to the patient 204 (FIGS. 2 and 3).

Returning to step 164, if no detection of the differentiating feature 106 of the patient interface assembly 104 is detected by the detection element 102, then the patient interface apparatus 112 does not fall within the predetermined category such that it is not recognized, as indicated at step 172. In the example of FIG. 5, the method 160 includes the optional step 174 of deciding whether or not to perform a manual override of the respiration machine 110, in order to permit it to operate (i.e., at step 170) despite the fact that the patient interface apparatus 112 does not fall within the predetermined category. For example and without limitation, such manual override procedure could entail the entry of a specific password or code and/or the manual entry of one or more respiration machine operating parameters (e.g., without limitation, ventilation type and duration; manual selection from a list or menu patient interface apparatus). If no such manual override procedure is performed, or alternatively if no such option is available, the method 160 ends at step 176 with the respiration machine 110 being inoperable in conjunction with the unidentified patient interface apparatus (not shown).

The example method 160 of FIG. 5 also includes the option, at step 166, of manually selecting and/or entering patient interface operating parameters (e.g., without limitation, interface apparatus type; therapy type and/or duration), which occurs at step 178 prior to operating (i.e., at step 170) the respiration machine 110, as opposed to having an automatic patient interface apparatus compensation routine conducted, as previously discussed.

Accordingly, the disclosed interface apparatus identification system 100 (FIG. 2), 100' (FIG. 3), 100" (FIG. 4) and method 160 (FIG. 5) provide for the relatively quick and easy control of a predetermined category (e.g., without limitation, specific brand or make) of patient interface apparatus (see, for example and without limitation, respiratory mask 112 of FIGS. 2 and 4; see also respiratory mask 112' of FIG. 3) which can be used in the desired manner with a particular respiration machine (see, for example and without limitation, medical ventilator 110 of FIG. 2; see also medical ventilators 110' and 110" of FIGS. 3 and 4, respectively).

While specific embodiments of the disclosed concept have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the disclosed concept which is to be given the full breadth of the claims appended and any and all equivalents thereof.

What is claimed is:

1. An interface apparatus identification method comprising steps of:
   (a) providing a patient interface assembly, the patient interface assembly comprising:
      (1) a patient interface apparatus adapted to deliver a flow of gas to an airway of a patient, the patient interface apparatus being selected from a predetermined category,
      (2) a detection element adapted to communicate with a respiration machine, the detection element comprising a photo eye adapted to detect fluorescence, and
      (3) a differentiating feature incorporated into the patient interface assembly, the differentiating feature being a material property of at least one component of the patient interface assembly, the material property being a fluorescence of a predetermined color triggered by exposure to light;
   (b) coupling the patient interface assembly to the respiration machine;
   (c) exposing the at least one component to light having a preselected wavelength;
   (d) responsive to said exposure, detecting with the photo eye the presence or absence of a fluorescence of a predetermined color, the patient interface assembly falling within the predetermined category if the fluorescence is present, the predetermined color being fixed with respect to the preselected wavelength,
   (1) if approving the patient interface apparatus for operation with the respiration machine,
   (2) if absent, prohibiting operation of the respiration machine absent a predetermined user input.

2. The method of claim 1, further comprising:
   (a) the detection element comprising the photo eye disposed proximate to a receptacle of the respiration machine,
   (b) the patient interface apparatus comprising a respiratory mask,
   (c) coupling the respiratory mask to the receptacle of the respiratory machine with at least one connector, and
   (d) responsive to the respiratory mask and the at least one connector being coupled to the receptacle, detecting with the photo eye the presence or absence of the differentiating feature.

3. The method of claim 2, further comprising steps of:
   (a) the at least one connector comprising a single connector,
   (b) connecting one end of the single connector directly to the receptacle of the respiration machine, and
   (c) connecting the respiratory mask directly to the other end of the single connector.

4. The method of claim 2, further comprising steps of:
   (a) providing the patient interface assembly with a conduit,
   (b) providing as the at least one connector a first connector and a second connector,
   (c) connecting a first end of the conduit to the receptacle of the respiration machine with the first connector, and
   (d) connecting the second end of the conduit to the respiratory mask with the second connector.

5. The method of claim 1, further comprising steps of:
   (a) responsive to the differentiating feature being detected, performing a patient interface apparatus compensation routine,
   (b) responsive to the compensation routine, synchronizing a number of operating characteristics of the respiration machine with the patient interface apparatus, and
   (c) operating the respiration machine in conjunction with the patient interface apparatus.

6. The method of claim 1, further comprising steps of:
   (a) responsive to the differentiating featuring not being detected, performing as said predetermined user input, a manual override of the respiration machine,
   (b) manually selecting a number of operating characteristics of the respiration machine, and
   (c) operating the respiration machine based upon said manually selected operating characteristics.

* * * * *